United States Patent [19]

Fernholz et al.

[11] 3,939,199

[45] Feb. 17, 1976

[54] OXACYLATION OF OLEFINS IN THE GASEOUS PHASE

[75] Inventors: Hans Fernholz, Fischbach, Taunus; Friedrich Wunder, Florsheim am Main; Hans-Joachim Schmidt, Falkenstein, Taunus, all of Germany

[73] Assignee: Hoechst Aktiengesellschaft, Frankfurt am Main, Germany

[22] Filed: June 22, 1973

[21] Appl. No.: 372,686

Related U.S. Application Data

[63] Continuation-in-part of Ser. No. 215,901, Jan. 6, 1971, abandoned.

[30] Foreign Application Priority Data

Jan. 8, 1971   Germany............................ 2100778

[52] U.S. Cl.......... 260/469; 252/431 C; 260/468 R; 260/497 A
[51] Int. Cl.²......................................... C07C 67/04
[58] Field of Search......... 260/497 A, 468 R, 469 R

[56] References Cited

UNITED STATES PATENTS

| | | | |
|---|---|---|---|
| 3,759,839 | 9/1973 | Fernholz | 260/497 A |
| 3,775,342 | 11/1973 | Kronig | 260/497 A |

FOREIGN PATENTS OR APPLICATIONS

| | | | |
|---|---|---|---|
| 6,807,752 | 5/1969 | South Africa | 260/497 A |
| 1,296,138 | 5/1969 | Germany | 260/497 A |

*Primary Examiner*—James A. Patten
*Assistant Examiner*—Killos
*Attorney, Agent, or Firm*—Curtis, Morris & Safford

[57] ABSTRACT

An improved process for oxacylating olefins in the gaseous phase which comprises using a supported catalyst comprising palladium and a carrier having a total pore volume of from 0.4 to 1.2 ml/g, less than 10% of the total pore volume being attributable to micropores having a diameter of less than 30 A. Catalysts of this type are much more efficient than conventional catalysts.

1 Claim, 1 Drawings

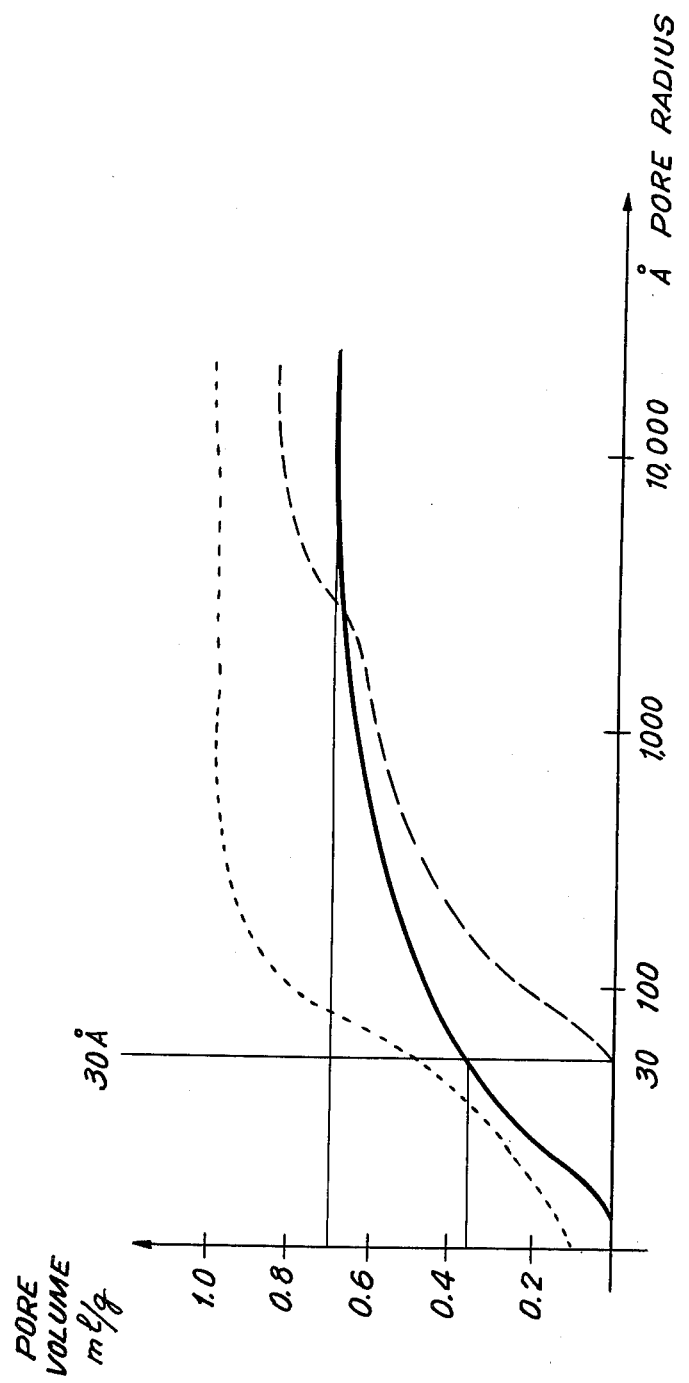

OXACYLATION OF OLEFINS IN THE GASEOUS PHASE

The present application is a continuation-in-part of application Ser. No. 215,901 filed 6th Jan., 1971, now abandoned.

The present invention relates to a process for oxacylating olefins in the gaseous phase in the presence of catalysts containing palladium.

It has been proposed to react olefins in the gaseous phase with organic carboxylic acids and oxygen or gases containing oxygen to yield oxacylation products, such as vinyl acetate, allyl acetate, or methally acetate. The reaction is preferably carried out in the presence of supported catalysts containing palladium or palladium salts and additives such as gold, gold salts, cadmium, cadmium salts, bismuth, bismuth salts, alkaline earth metal salts and alkali metal salts. In general, the active components are applied to a porous carrier such as silicic acid, aluminum oxide, aluminum silicates, titanium oxide, zirconium oxide, silicates, silicium carbide, or carbon.

The present invention provides a process for oxacylating olefins in the gaseous phase wherein an olefin selected from the group consisting of ethylene, propylene and isobutylene is reacted with oxygen and an organic carboxylic acid in the presence of a catalyst consisting essentially of palladium or palladium salts and an additive selected from the group consisting of gold, gold salts, cadmium, cadmium salts, bismuth, bismuth salts, alkaline earth metal salts and alkali metal salts, supported on a porous carrier selected from the group consisting of silicic acid, aluminum silicate, titanium oxide, zirconium oxide, silicates and glasses, and having a total pore volume of from 0.4 to 1.2 ml/g, and wherein the total pore volume attributable to pores having a diameter less than 30 A is less than 10% of the total pore volume.

By using a carrier of this type the efficiency of the catalyst can be substantially improved with an identical content of active components and under identical reaction conditions. Hence, the advantages of the process of the invention reside in the fact that when new plants are constructed smaller catalyst amounts and reactor volumes are sufficient so that the construction costs can be considerably reduced, or, in the case of existing plants, the capacity can be greatly improved without any reconstruction whereby investment costs for an enlargement of the plants can be saved.

Suitable carrier materials are the usual inert substances such as silicic acid, silicates, aluminum silicates, titanium oxide, zirconium oxide, and various glasses.

To avoid the formation of micropores it is recommended to use molten particles without inner pores and having a mean particle diameter which is generally not below 80 A. Vitreous molten small particles have almost always the shape of a sphere, and, therefore, the smallest pore diameter results from the closest sphere packing. An upper limit for the average particle diameter depends on the necessary lower limit for the total surface of the carrier. As the lower limit is approximately the sum of the individual particle surfaces and should not fall below 40 $m^2/g$, the average particle size will not be substantially above 600 A to 1,000 A.

These particles without pores can be obtained, for example, by hydrolysis of silicium, zirconium and titanium tetrachloride in a hydrogen-air or oxyhydrogen flame. The particles can also be produced by melting micronized substances, such as aluminum silicate, silica gel, or glass under conditions avoiding the formation of larger droplets and hence a reduction of the total surface of the carrier below a value of 40 $m^2/g$, for example by blowing the particles with a current of air or inert gas through a sufficiently hot flame and allowing them to cool below their melting point prior to collection.

From these small particles larger balls, tablets or granules suitable for the manufacture of catalysts can be produced in various ways, for example by making a paste of the powdery mass with a dilute solution of a mineral glue, extruding or molding the paste into pellets, granules, or tablets having the desired shape and transforming the glue into a difficultly soluble form by burning. Suitable inorganic glues are, for example, water glass, silicic acid sol, aluminum oxide sol, kaolin, or bentonite. Alternatively, the particles made into a paste with an aqueous sol can be suspended in a solvent or diluent immiscible with water and the sol can be allowed to gel, whereby especially porous products are obtained. Another method consists in spraying a thin paste of the particles in a sol through a nozzle and allowing the sol to gel in the free fall. In order to avoid damage of the gelled and still soft particles, they can be sprayed in upward inclined direction and collected in a liquid bath (for example water) or they can be conducted in countercurrent flow with a current of air or gas which reduces their impact velocity and simultaneously improves their resistance by drying. In this manner particles of almost any desired size can be produced.

The carriers thus obtained are impregnated with the active components in usual manner. In a process for oxacetylizing ethylene to vinyl acetate they are impregnated, for example, with a solution of palladium acetate, cadmium acetate and potassium acetate in acetic acid with subsequent drying and when propylene is oxacetylized to yield allyl acetate or isobutylene to yield methallyl acetate they are impregnated, for example, with a solution of palladium acetate, gold acetate, bismuth acetate, and potassium acetate in acetic acid, and subsequently dried.

The oxacylation in the presence of the palladium containing catalyst is effected by passing carboxylic acid, olefin and oxygen or gases containing oxygen over the catalyst at a temperature in the range of from 100° to 250°C under a pressure of from 1 to 10 atmospheres, unreacted reaction components possibly being conducted in a cycle.

The concentrations of the reaction components should be chosen in such a manner that the reaction mixture is outside the known explosion limits. This can be achieved most simply by keeping low the oxygen concentration, for example, in the range of from 3 to 8% of the gases used. Under these conditions a dilution with inert gases, for example nitrogen or carbon dioxide, may, however, also be advantageous.

The olefins to be used in the process of the invention are ethylene, propylene, and isobutylene.

In the process of the invention saturated aliphatic, cycloaliphatic, araliphatic or aromatic carboxylic acids having one or several carboxyl groups can be reacted. It is essential, however, that the carboxylic acids used are vaporizable under the reaction conditions, therefore, their number of carbon atoms will generally not exceed 10. There are preferably reacted unsubstituted, saturated aliphatic monocarboxylic acids having 2 to 4 carbon atoms, for example propionic acid, n-butyric acid, and isobutyric acid, acetic acid being preferred. The carboxylic acids may also be used in the form of aqueous solutions. The reaction is preferably carried out in the presence of one or several alkali metal salts of the carboxylic acid to be reacted, advantageously sodium salts and potassium salts and more advantageously potassium salts. The alkali metal carboxylates are preferably used in an amount of from 0.1 to 10% by weight, calculated on the weight of the catalyst consisting of carrier material and catalytically active substances.

According to an especially favorable mode of execution of the process of the invention the alkali metal salts of the carboxylic acids are continuously or discontinuously added to the catalyst during the course of reaction, in an amount of from 0.1 to 400 ppm, preferably 1 to 100 ppm, calculated on the carboxylic acid used.

The process of the invention can be carried out in fixed bed or fluidized bed reactors, in general the fixed bed being preferred.

In the following table are indicated the results of reactions carried out with two types of conventional carriers and a carrier without micropores according to the invention, which clearly show the advantage of the latter.

pore volume is the limiting value the integral pore volume approaches for growing pore radii.

The integral pore volume for pores of a definite minimum size can be determined with the aid of the mercury porosimetry which is based on the capillary depression of mercury. The pressure exerted on mercury with this method is inversely proportional to the radius of the smallest pores into which mercury can be forced under the given pressure. The amount of mercury taken up by pores of a determined radius with a small increase in pressure corresponds to the percentage of the total pore volume attributable to the said pores.

In order to measure the percentage of the total pore volume which is attributable to micropores a similar method is used which is based on the capillary condensation of argon or nitrogen in the micropores.

The following examples illustrate the invention. They were carried out in an apparatus with reactors in parallel connection to permit comparison of different catalysts under identical reaction conditions. The reactors allowed of a straight passage of the reaction components. The results obtained are only comparative results under the same reaction conditions. They do not represent maximum results obtainable under different conditions, for example in a process operating with cycle gas or in a fluidized bed. The gaseous components were measured under normal conditions of pres- Table

| reaction product | conventional silica gel carrier with 1.0 ml/g pore volume, 50% of total pore volume attributable to micropores with a diameter ≤ 30A | conventional SiO$_4$ stratified lattice carrier with 0.73 ml/g pore volume, 45% of total pore volume attributable to micropores with a diameter ≤ 30 A | carrier of invention with 0.35 ml/g pore volume, no micropores |
|---|---|---|---|
| vinyl acetate | 215 g/l.h | 220 g/l.h | 305 g/l.h |
| allyl acetate | 180 g/l.h | 190 g/l.h | 280 g/l.h |
| methallyl acetate | 185 g/l.h | 170 g/l.h | 270 g/l.h |
| allyl propionate | 173 g/l.h | 180 g/l.h | 265 g/l.h |

The considerable increase in efficiency obtained with the use of carriers which are almost free from micropores having a diameter below 30 A is surprising and could not have been foreseen as the effective molecule diameters are much lower, i.e. in the range of from 4 A to 6 A for example:

| effective diameter of oxygen | 2.8 A |
| effective diameter of carbon dioxide | 2.8 A |
| effective diameter of ethylene | 4.2 A |
| effective diameter of propylene | 5.0 A |
| effective diameter of isobutylene | 5.6 A |

Hence, the lower efficiency of the conventional carriers cannot be explained by the fact that part of the specific surface is not accessible to the reactants. Moreover, it is known that molecular sieves having a pore width of 10 A are especially good catalysts, even for the manufacture of bulky molecules, such as di-isopropylbenzene from benzene and propylene so that a steric hindrance of the reaction in the small pores is unlikely.

The total pore volume of a porous carrier material can be measured according to a standard method by the amount of liquid argon or nitrogen absorbed by a determined amount of carrier material.

The so-called "integral pore volume" is a measurement of the percentage of the total pore volume which is attributable to pores of a certain dimension. The total sure and temperature.

The drawing shows the proportion of pores of different diameters with respect to the total pore volume of the carriers used in the Examples. The function I relates to the carrier according to the invention and shows that in this carrier no micropores with a diameter of less than 30 A are present. This carrier is used in Examples 1c, 2c, and 3c.

The functions II and III relate to the conventional carriers used in Examples 1b, 2b, 3b, and Examples 1a, 2a, 3a, respectively. As regards the carrier used in Examples 1a, 2a, 3a (III), the pore volume function attains 50% (i.e. 0.35 ml/g) of its final value (i.e. 0.7 ml/g) at a pore diameter of 30 A, i.e. 50% of the total pore volume of this carrier is attributable to micropores. The corresponding value for the carrier used in Examples 1b, 2b, 3b, (II) is 45%.

EXAMPLE 1

Vinyl acetate from ethylene, acetic acid and oxygen

1a. Comparative example using a conventional carrier on the basis of silica gel.

1 Liter, corresponding to 400 grams, of a granular silica gel catalyst having a specific surface of 350 m$^2$/g, a pore volume of 1.0 ml/g and a grain size of 2.5 to 7 mm was used. 50% of the total pore volume of the carrier is attributable to micropores with a diameter ≤ 30 A. The carrier was impregnated with a solution of
- 10.7 grams of palladium acetate
- 19 grams of cadmium acetate
- 20 grams of potassium acetate in
- 370 milliliters of acetic acid and dried.

1 Liter of the catalyst obtained was filled into a reaction tube having an inner diameter of 32 millimeters. Under a pressure of 5 atmospheres gage and at an inside temperature of 180°C a mixture consisting of 850 liters of ethylene, 75 liters of oxygen and 870 grams of acetic acid was passed per hour over the catalyst. Under these conditions a catalyst yield of 215 grams of vinyl acetate was obtained per hour.

1b. Comparative example using a conventional carrier on the basis of a silicic acid layer lattice.

1 Liter, corresponding to 564 grams, of a silicic acid carrier having a specific surface of 160 m²/g, a pore volume of 0.73 ml/g, and a sphere size of 6 mm was used. 45% of the total pore volume of the carrier is attributable to micropores with a diameter ≤ 30 A. The carrier was impregnated with a solution of
- 10.7 grams of palladium acetate
- 19 grams of cadmium acetate
- 20 grams of potassium acetate in
- 395 milliliters of acetic acid and dried.

Under the conditions specified in Example 1a ethylene, oxygen and acetic acid were reacted using 1 liter of the catalyst so obtained. The catalyst yield amounted to 220 grams of vinyl acetate per hour.

1c. Example according to the invention using a silicic acid carrier which was practically free from micropores having a diameter below 30 A.

1 Liter of a silicic acid carrier, corresponding to 450 grams, which was free from micropores, had a specific surface of 205 m²/g and a pore volume of 0.85 ml/g. The carrier was impregnated with a solution of
- 10.7 grams of palladium acetate
- 19 grams of cadmium acetate and
- 20 grams of potassium acetate in
- 350 milliliters of acetic acid and dried.

Under the conditions specified in Examples 1a and 1b the same amounts of ethylene, oxygen and acetic acid were passed over 1 liter of the catalyst thus obtained. A catalyst yield of 305 grams of vinyl acetate was obtained per hour.

EXAMPLE 2

Allyl acetate from propylene, acetic acid and oxygen

2a. Comparative example using the same conventional silica gel carrier as in Example 1a.

1 Liter, corresponding to 400 grams, of the carrier was impregnated with a solution of
- 10.7 grams of palladium acetate
- 6.5 grams of barium acetoaurate (III)
- 5.9 grams of bismuth acetate and
- 46 grams of potassium acetate in
- 360 milliliters of acetic acid and dried.

1 Liter of the catalyst obtained was filled into the reactor described in Example 1a and under a pressure of 5 atmospheres gage and at 180°C a mixture of 850 liters of propylene, 75 liters of oxygen and 870 grams of acetic acid was passed per hour over the catalyst.

Under the specified conditions a catalyst yield of 180 grams of allyl acetate was obtained per hour.

2b. Comparative example using the same conventional carrier on the basis of a silicic acid layer lattice as in Example 1b.

1 Liter of the carrier, corresponding to 564 grams was impregnated with a solution of
- 10.7 grams of palladium acetate
- 6.5 grams of barium acetoaurate (III)
- 5.9 grams of bismuth acetate and
- 46 grams of potassium acetate in
- 365 milliliters of acetic acid and dried.

Propylene, oxygen and acetic acid in the amounts specified in Example 2a were passed under the conditions specified in said example over 1 liter of the catalyst obtained. A catalyst yield of 190 grams of allyl acetate was obtained per hour.

2c. Example according to the invention using the same silicic acid carrier as in Example 1c practically free from micropores having a diameter below 30 A.

1 Liter of the carrier, corresponding to 450 grams, was impregnated with a solution of
- 10.7 grams of palladium acetate
- 6.5 grams of barium acetoaurate (III)
- 5.9 grams of bismuth acetate and
- 46 grams of potassium acetate in
- 340 milliliters of acetic acid and dried.

Under the conditions specified in Examples 2a and 2b propylene, oxygen and acetic acid were passed in the same amounts as in said examples over 1 liter of the catalyst obtained. The catalyst yield in this example was 280 grams of allyl acetate per hour.

EXAMPLE 3

Methallyl acetate from isobutylene, acetic acid and oxygen

3a. Comparative example using the same conventional silica gel carrier as in Examples 1a and 2a.

1 Liter of the catalyst specified in Example 2a was filled into the reactor described in Example 1a) and under a pressure of 5 atmospheres gage and at 180°C a mixture of 850 liters of isobutylene, 75 liters of oxygen and 870 grams of acetic acid was passed per hour over the catalyst. Under the specified conditions a catalyst yield of 185 grams of methallyl acetate was obtained per hour.

3b. Comparative example using the same conventional carrier on the basis of a silicic acid layer lattice as in Examples 1b and 2b.

Isobutylene, oxygen and acetic acid were passed over 1 liter of the catalyst specified in Example 2b under the conditions and in the amounts indicated in Example 3a. A catalyst yield of 170 grams of methallyl acetate was obtained per hour.

3c. Example according to the invention using the same silicic acid carrier as in Examples 1c and 2c practically without micropores having a diameter below 30 A.

Under the conditions and in the amounts specified in Examples 3a and 3b isobutylene, oxygen and acetic acid were passed over 1 liter of the catalyst defined in Example 2c. A catalyst yield of 270 grams of methallyl acetate was obtained per hour.

EXAMPLE 4

Allyl propionate from propylene, propionic acid and oxygen

4a. Comparative example using the same conventional silica gel carrier as in Examples 1a, 2a, and 3a.

Under a pressure of 5 atmospheres gage and at 180°C a mixture of 850 liters of propylene, 75 liters of oxygen and 1075 grams of propionic acid was passed per hour over 1 liter of the catalyst specified in Example 2a. 173 grams of allyl propionate were obtained per hour.

4b. Comparative example using the same conventional carrier on the basis of a silicic acid layer lattice as in Examples 1b, 2b and 3b.

Under the conditions and in the amounts specified in Example 4a propylene, oxygen and propionic acid were passed over 1 liter of the catalyst described in Example 2b. 180 Grams of allyl propionate were obtained per hour.

4c. Example according to the invention using the same silicic acid carrier as in Examples 1c, 2c, 3c practically free from micropores below 30 A.

Propylene, oxygen and propionic acid were passed under the conditions and in the amounts specified in Examples 4a and 4b over 1 liter of the catalyst defined in Example 2c. The catalyst yield amounted to 265 grams of allyl propionate per hour.

What is claimed is:

1. In a process for oxacylating olefins in the gaseous phase wherein an olefin selected from the group consisting of ethylene, propylene and isobutylene is reacted with oxygen and a saturated aliphatic, cycloaliphatic, araliphatic or aromatic carboxylic acid having not more than 10 carbon atoms in the presence of a catalyst consisting essentially of palladium or palladium salts and an additive selected from the group consisting of gold, gold salts, cadmium, cadmium salts, bismuth, bismuth salts, alkaline earth metal salts and alkali metal salts, supported on a porous silicic acid carrier, the improvement which comprises: using a silicic acid support for said catalyst having a total pore volume of from 0.4 to 1.2 ml/g wherein the total pore volume attributable to pores having a diameter less than 30 A is less than 10% of the total pore volume.

* * * * *